(12) United States Patent
Cleary (10) Patent No.: US 6,589,051 B2
(45) Date of Patent: Jul. 8, 2003

(54) MECHANISM WITH FORMED STOP FOR LIMITING RELATIVE MOVEMENT

(75) Inventor: James D. Cleary, Glendora, CA (US)

(73) Assignee: 3M Innovative Properties Company, St. Paul, MN (US)

( * ) Notice: Subject to any disclaimer, the term of this patent is extended or adjusted under 35 U.S.C. 154(b) by 2 days.

(21) Appl. No.: 09/912,911

(22) Filed: Jul. 25, 2001

(65) Prior Publication Data

US 2003/0022125 A1 Jan. 30, 2003

(51) Int. Cl.[7] .......................... A61C 3/00; A63H 17/26; F16D 1/00
(52) U.S. Cl. .......................... 433/19; 446/469; 403/112
(58) Field of Search .............................. 401/109, 117; 403/109.2, 112, 245, 246, 359, 360, 375, 383, 387; 81/177.2, 489; 29/515, 516, 517; 446/469; 433/19

(56) References Cited

U.S. PATENT DOCUMENTS

| | | | | |
|---|---|---|---|---|
| 2,597,588 A | * | 5/1952 | Manoil | 280/11.19 |
| 2,972,781 A | * | 2/1961 | Levy | 264/320 |
| 3,162,082 A | * | 12/1964 | Anderson | 403/360 |
| 3,612,668 A | * | 10/1971 | Watkins | 351/118 |
| 3,798,773 A | | 3/1974 | Northcutt | |
| 5,230,134 A | | 7/1993 | Laue | |
| 5,562,445 A | * | 10/1996 | DeVincenzo et al. | 433/18 |
| 5,711,667 A | | 1/1998 | Vogt | 433/19 |
| 5,964,588 A | | 10/1999 | Cleary | |

FOREIGN PATENT DOCUMENTS

EP 0 074 765 3/1983

OTHER PUBLICATIONS

Pending U.S. patent application Ser. No. 09/687,392, filed Oct. 13, 2000.
Pending U.S. patent application Ser. No. 09/912,766, filed Jul. 25, 2001.
Groove–Pin™ fastener brochure, undated, from Groove–Pin Corporation, 4 pages.

* cited by examiner

Primary Examiner—Cary E. O'Connor
(74) Attorney, Agent, or Firm—James D. Christoff (57) ABSTRACT

A mechanism includes a first member having a channel and a second member with a generally cylindrical portion at least partially received in the channel. The second member includes a stop portion for limiting relative movement of the first member and the second member. The stop portion is made of a formable material and includes at least three lobes that extend outwardly in different respective directions. The stop portion increases the stiffness of the second member, and is useful in both pivoting and rotating mechanisms for limiting relative movement between the first member and the second member.

27 Claims, 4 Drawing Sheets

MECHANISM WITH FORMED STOP FOR LIMITING RELATIVE MOVEMENT

BACKGROUND OF THE INVENTION

1. Field of the Invention

This invention relates to a mechanism having an elongated member such as a shaft, plunger or rod that has been formed to present a stop. The stop prevents relative movement between the member and another component of the mechanism in directions parallel to the longitudinal axis of the member.

2. Description of the Related Art

Many types of mechanisms in common use include a stop for limiting relative movement between one member and another member of the mechanism. In some instances, the stop is provided to prevent disengagement and separation of the members from each other. In other instances, the stop is provided to limit relative movement of the two members to a range that is deemed desirable for satisfactory performance of the mechanism.

For example, some rotating mechanisms have a first member that is a wheel, drum, roller or pulley and have a second member that extends through the first member. The second member may be a shaft, axle or rod or other type of component. The two members are movable relative to each other in arcs that extend about the longitudinal axis of the second member. For example, the first member may be stationary while the second member revolves, or the second member may be stationary while the first member revolves. In some instances, both of the members are freely rotatable in directions about the longitudinal axis of the second member.

In the rotating mechanism described above, one or more stops are often provided for limiting relative movement of the two members in directions parallel to the longitudinal axis of the second member. For example, a pair of cylindrical sleeves might be fixed to a shaft on opposite sides of a wheel to keep the wheel in place and prevent the wheel from disengaging the shaft. In those instances, the sleeves permit free relative pivotal movement of the wheel and shaft in directions about the longitudinal axis of the shaft, but limit the extent of sliding movement of the wheel in directions parallel to the longitudinal axis of the shaft.

Other examples of mechanisms with stops include various types of sliding mechanisms. A sliding mechanism may include, for instance, a first member having a channel and a second member that is partially received in the channel. The members are movable relative to each other in directions parallel to the longitudinal axis of the second member. For instance, the second member may slide along the channel while the first member is stationary, or the first member may slide along the length of the second member while the second member is stationary. In other instances, both of the members may be freely movable.

One well-known example of a sliding mechanism is a telescoping-type of mechanism where the channel of the first member has a shape that surrounds and is complemental to the shape of the second member when considered in reference planes that are perpendicular to the longitudinal axis of the second member. In those mechanisms, the second member may be provided with one or more stops to limit relative sliding movement. For instance, the second member may have a stop that is intended to prevent the second member from moving out of the channel and disengaging the first member. In other instances, the second member may have a stop that limits sliding movement for other reasons that are deemed necessary or practical for satisfactory operation of the mechanism.

An example of a telescoping mechanism having a stop is described in U.S. Pat. No. 5,964,588, assigned to the assignee of the present invention. The mechanism described in that patent is an intra-oral device for applying a force to the upper and lower dental arches of a patient undergoing orthodontic treatment, and includes a spring that tends to move the relative positions of the upper and lower dental arches when the patient's jaws are closed.

The force module described in U.S. Pat. No. 5,964,588 includes a collar that is mounted on one member. The collar functions as a stop to limit sliding movement of two members relative to each other. The position of the collar on the member can be selected by the orthodontic practitioner so that the spring provides the desired amount of biasing force when the patient's jaws are closed. In certain embodiments of the force module described in that patent, the collar is in the shape of a cylindrical sleeve that is fixed to the member by, for example, a welding, brazing or crimping operation.

Over the years, there has been a continuing interest in reducing manufacturing costs, including the costs of making various types of moving mechanisms. As a result, efforts have been directed to simplify the manufacture of stops that are present in movable mechanisms. In this regard, the provision of a stop can add considerable expense to the cost of manufacturing a mechanism, even though the function of the stop may be deemed relatively simple.

For example, the manufacture of the orthodontic force module described in the aforementioned U.S. Pat. No. 5,964,588 may include several steps related to the stop or collar. For instance, the method may include the step of cutting a section of tubular cylindrical stock to a desired length to make a stop or collar. Next, both the collar and the member receiving the collar are cleaned as needed. The collar is then positioned at an appropriate place along the length of the member and is tack-welded in place to hold its position. The collar is then brazed to the member in an oven to provide a strong, secure connection between the collar and the member. Finally, the collar and member are cleaned and assembled to remaining components of the force module.

By contrast, some movable mechanisms have stops that are integral with one of the members. As can be appreciated, such construction avoids the need to manufacture and assemble two separate components. Optionally, the manufacture of integral stops is carried out in automated fashion, so that the stop is automatically placed at its desired location along the length of the member in each instance.

One common example of a movable mechanism with an integral stop is a toy vehicle having a wheel that is mounted on a cylindrical shaft. The ends of the shaft are deformed during manufacture to a flattened configuration. The increased width of the flattened ends in directions perpendicular to the longitudinal axis of the shaft is greater than the diameter of the hole in the wheel. Consequently, the flattened ends of the shaft prevent the wheel from disengaging the shaft. However, the wheel is located over the cylindrical portion of the shaft and can turn as needed about the longitudinal axis of the shaft.

The flattened, integral stop as described above is satisfactory for use in many types of mechanisms, especially in mechanisms where substantial forces are not expected to be encountered. However, in other instances, the presence of substantial forces may cause the mechanism to fail. Such a failure is particularly problematic in instances where it is not desirable or practical to simply increase the size of the members to increase their strength.

The telescoping intra-oral force module described in U.S. Pat. No. 5,964,588 may encounter significant forces in use. For example, significant forces may be imposed on the force module during mastication, especially when the patient is chewing a relatively hard food object. If the flattened stop described above is substituted for the collar stop, the resulting assembly may bend or break during use and prompt the patient to return to the orthodontist's office for repair or replacement. As can be appreciated, such a failure represents a nuisance to both the practitioner and the patient in terms of time and expense.

Moreover, it would not be deemed desirable to simply increase the overall size of the orthodontic force module members in the hypothetical example described above in order to avoid such failures. The space in the oral cavity is somewhat limited and is occupied by other components of the orthodontic system as well, including brackets and archwires. An increase in size of the force module may cause the force module to impinge on the patient's soft tissue adjacent the cheeks and lips, resulting in discomfort.

From the foregoing, it can be appreciated that there is a need in the art for an improved stop for a movable mechanism that does not unduly increase the cost or size of the mechanism or increase the likelihood that the mechanism will fail during use.

SUMMARY OF THE INVENTION

The present invention is directed to a movable mechanism having stop that is integrally formed in one member of the mechanism. The stop is made by forming at least three impressions in the member that are spaced apart from each other when considered in reference planes perpendicular to the longitudinal axis of the member. The impressions so formed result in three or more distinct lobes that extend outwardly from the longitudinal axis a distance sufficient to function together as a stop.

Surprisingly, it has been found that the resulting stiffness of the member is increased about multiple reference axes in sections of the member where the lobes are present in comparison to remaining sections of the member that lack the lobes. As such, the resulting mechanism is less likely to fail in use, regardless of the direction of the imposed force.

The present invention is a substantial advantage over mechanisms having stops that are made by flattening opposite sides of a cylindrical member to present two oppositely-extending lobes. In the latter instance, the stiffness of the member is increased in the direction of extension of the lobes but is decreased in perpendicular directions. As a result, that stop may bend or fracture if substantial forces are encountered in the latter directions.

In more detail, the present invention in one aspect is directed to a mechanism that comprises a first member having a channel and a second member having a generally cylindrical portion at least partially received in the channel. The cylindrical portion has a longitudinal axis. The first member and the second member are movable relative to each other in directions along the longitudinal axis. The second member also has a stop portion for limiting relative movement between the first member and the second member in directions along the longitudinal axis. The stop portion is made of a formable material and the material is formed to present at least three lobes that extend outwardly in different respective directions from the longitudinal axis.

Another aspect of the invention is directed to a sliding mechanism. The mechanism includes a receiving member having a channel and a plunger having a generally cylindrical portion at least partially received in the channel. The cylindrical portion has a longitudinal axis. The plunger and the receiving member are slidably movable relative to each other in directions along the length of the longitudinal axis. The plunger also has a stop portion for limiting relative sliding movement between the plunger and the receiving member. The stop portion is made of a formable material and the material is formed to present at least three lobes that extend outwardly in different respective directions from the longitudinal axis.

The present invention is also directed to a rotating mechanism. In this aspect, the mechanism includes a first member having a channel and a second member having a generally cylindrical portion at least partially received in the channel. The cylindrical portion has a longitudinal axis. The first member and the second member are rotatable relative to each other in directions about the longitudinal axis. The second member also has a stop portion for limiting relative sliding movement between the first member and the second member in directions along the longitudinal axis. The stop portion is made of a formable material and the material is formed to present at least three lobes that extend outwardly in different respective directions from the longitudinal axis.

An additional aspect of the present invention is related to an intra-oral force module for moving the relative positions of the upper and lower dental arches. The force module comprises a first member having a channel and a second member having a generally cylindrical portion at least partially received in the channel. The cylindrical portion has a longitudinal axis. The first member and the second member are slidable relative to each other in directions along the length of the longitudinal axis. The second member also includes a stop portion for limiting relative sliding movement of the first member and the second member. The stop portion is made of a formable material and the material is formed to present at least three lobes that extend outwardly in different respective directions from the longitudinal axis.

Other aspects, features and advantages of the present invention are described in the paragraphs that follow and are illustrated in the accompanying drawings.

DETAILED DESCRIPTION OF THE PREFERRED EMBODIMENTS

Figure 1:
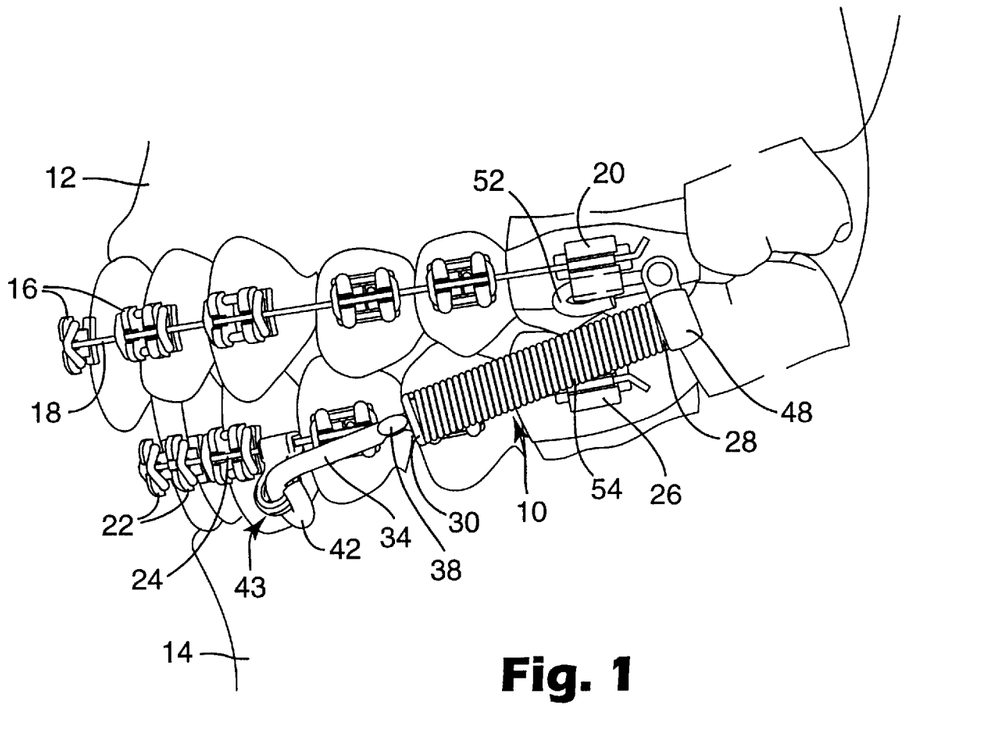
FIG. 1 is a side view in partially schematic form of a mechanism according to one embodiment of the invention, wherein in this instance the mechanism is an intra-oral force module that has been installed in the oral cavity of a patient undergoing orthodontic treatment.

A mechanism according to one embodiment of the invention is illustrated in FIGS. 1–5 and 8 and is broadly designated by the numeral 10. In this embodiment, the mechanism 10 is an intra-oral force module useful for moving dental structure in the oral cavity. In FIG. 1, the mechanism 10 is shown as it might appear when connected to an exemplary upper dental arch 12 and an exemplary lower dental arch 14 of a patient that is undergoing orthodontic treatment.

In FIG. 1, a set of upper orthodontic brackets 16 is mounted on the teeth of the upper dental arch 12. An elongated upper archwire 18 extends through slots of the upper brackets 16 as well as through a passage of an upper buccal tube 20 that is received on a molar tooth of the patient's upper dental arch 12. The upper archwire 18 is secured to the upper brackets 16 by elastomeric O-ring ligatures as shown in the drawings, although other types of ligatures could be used as well.

A set of lower orthodontic brackets 22 is mounted on the teeth of the lower dental arch 14 in FIG. 1. An elongated lower archwire 24 extends through slots of the lower brackets 22. The lower archwire 24 also extends through a passage of a lower buccal tube 26 that is secured to a lower molar tooth in the lower dental arch 14. In this example, elastomeric O-ring ligatures are also used to secure the lower archwire 24 to the lower brackets 22.

The mechanism or force module 10 is shown in FIG. 1 as it might be installed for repositioning the lower dental arch 14 relative to the upper dental arch 12. In particular, the force provided by the mechanism 10 according to the example shown in FIG. 1 tends to move the lower dental arch 14 in a forward direction relative to the upper dental arch 12 when the patient's jaws are closed in order to correct what is known in the dental art as a Class II malocclusion. However, the mechanism 10 may also be used if desired for correcting other types of malocclusions or for repositioning the teeth along a single dental arch.

The mechanism 10 is shown in more detail in FIGS. 2–5 and 8 and includes a receiving member or first member 28 that is made of a section of tubular material having a cylindrical configuration. An annular fitting 30 is secured to one end of the first member 28. An opposite end of the first member 28 is slightly flared. The first member 28 is elongated and has internal cylindrical channel 32.

Figure 4:
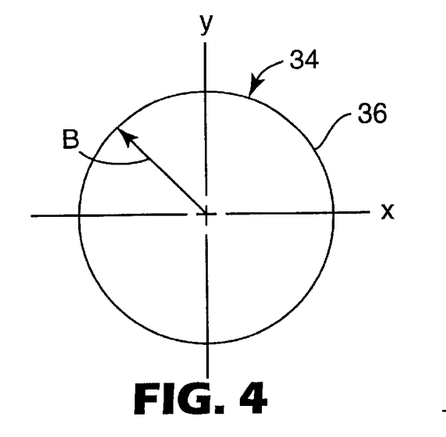
FIG. 4 is an enlarged end cross-sectional view taken along lines 4—4 of FIG. 2, and wherein additional components of the force module have been omitted for purposes of illustration.

The mechanism 10 also includes a plunger or second member 34 with a cylindrical portion 36 that is received in the channel 32. The first member 28 and the second member 34 are slidable relative to each other in directions along the longitudinal axis of the cylindrical portion 36. Preferably, the outer diameter of the cylindrical portion 36 and the inner diameter of the channel 32 are selected to provide a close, mating fit that allows free sliding movement in a longitudinal direction without excessive slop (i.e., movement in a lateral direction). A cross-sectional view of the cylindrical portion 36 alone is shown in FIG. 4.

Figure 5:
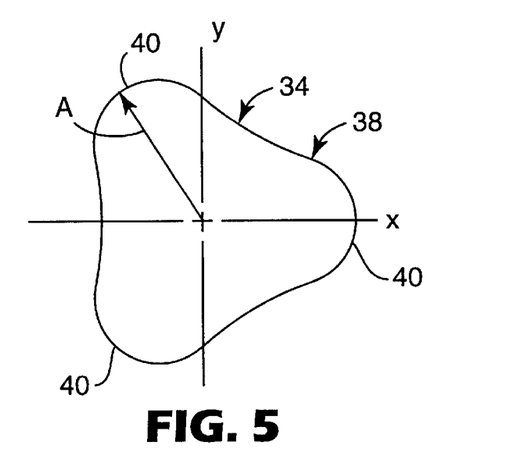
FIG. 5 is a view somewhat similar to FIG. 4 except that FIG. 5 illustrates a stop portion of the force module and is taken along lines 5—5 of FIG. 2.

The second member 34 also includes a stop portion 38 that is shown in enlarged end cross-sectional view in FIG. 5.

The stop portion 38 in this embodiment includes three lobes 40 that are arranged in a symmetrical manner in radial directions about the longitudinal axis of the cylindrical portion 36. In this embodiment, the lobes 40 are substantially identical in shape and extend outwardly from the longitudinal axis an equal distance, although other constructions are also possible.

The second member 34 including the stop portion 38 are made of a formable material. The three lobes 40 are made by squeezing a cylindrical section of material at three locations that are spaced equal distances apart around the periphery of the cylindrical section. Compression tooling, or a tool having three jaws, may be used to squeeze the cylindrical section at three locations to deform the material.

In FIG. 4, the cylindrical portion 36 as shown also represents the initial shape of the stop portion 38 before such time as the lobes 40 are formed. Consequently, the difference between the original configuration of the stop portion 38 and the resulting deformed configuration will become apparent by comparing FIG. 4 to FIG. 5. However, the actual shape of the lobes 40 may be different than that shown in FIG. 5 due to free flowing of the material during deformation.

The lobes 40 each extend radially outwardly from the longitudinal axis a distance that is labeled "A" in FIG. 5. In FIG. 4, the radius of the cylindrical portion 36 (which is also equal to the initial radius of the stop portion 38 before deformation) is identified by the letter "B". The dimension "A" exceeds the dimension "B" and also exceeds the inner radius of the channel 32 shown in FIGS. 2 and 3. As such, the lobes 40 limit the extent of relative movement between the first and second members 28, 34 and prevent the stop portion 38 from moving within the channel 32.

Figure 6:
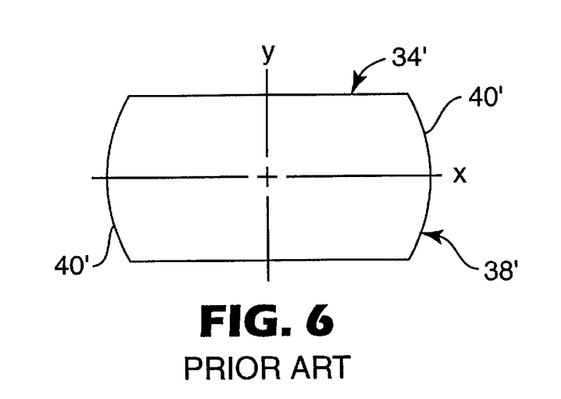
FIG. 6 is a hypothetical example for purposes of comparison, showing a prior art stop portion that is made by flattening a cylindrical member to present two lobes.

FIG. 6 shows for purposes of comparison an end cross-sectional view of a hypothetical member 34' that is made from a solid, cylindrical section of formable material. The second member 34' has a cylindrical portion as well as a stop portion 38'. In this instance, the stop portion 38' has been formed by squeezing opposite sides of the cylindrical section in order to deform the material and present two lobes 40'. The cylindrical portion is not shown, but has a radius equal to the radius "A" in FIG. 4.

Figure 2:
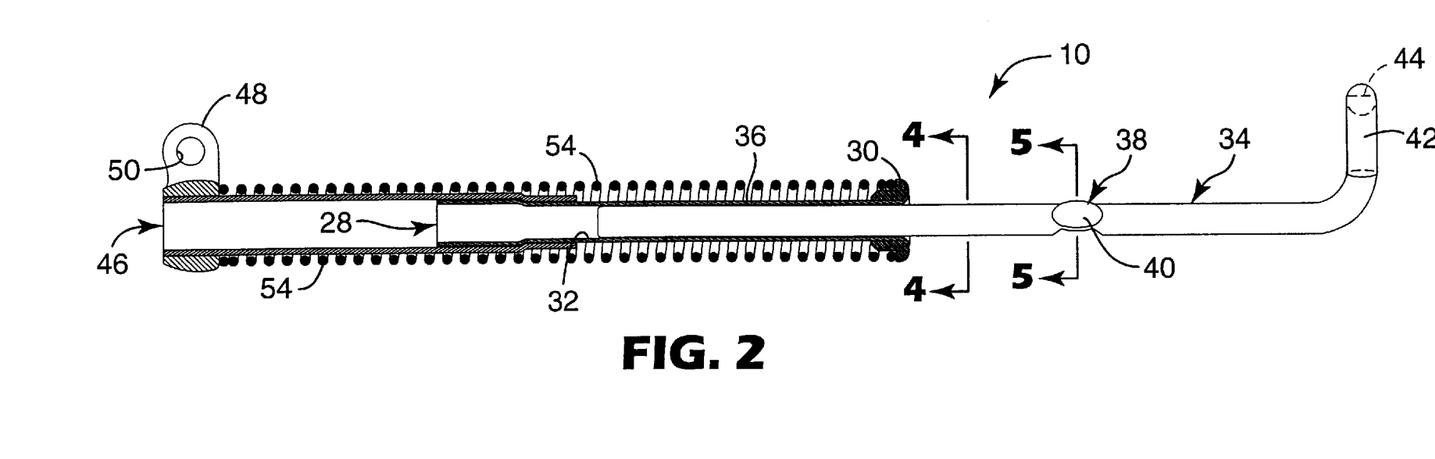
FIG. 2 is an enlarged side cross-sectional view of the force module alone that is illustrated in FIG. 1, except that in FIG. 2 the force module is shown in an extended configuration and from an opposite side.
Figure 3:
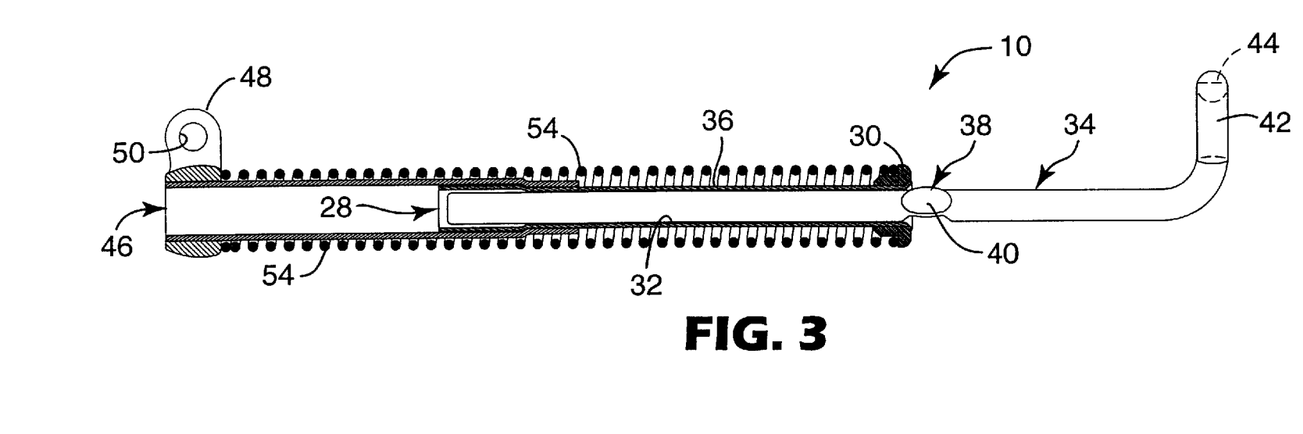
FIG. 3 is a view somewhat similar to FIG. 2 except that in FIG. 3 one member of the force module has been moved to a position that is different than its position shown in FIG. 2.

The construction shown in FIG. 6 is designated "Prior Art" because it is a formed stop that is known for use in various mechanisms. However, it should be mentioned that use of the formed stop shown in FIG. 6 with the particular mechanism shown in FIGS. 1–3 is not known to applicant.

For purposes of comparison, the moments of inertia ("I") were calculated for the stop portions 38, 38' and also for the initial cylindrical shape of the stop portions 38, 38' before deformation. For this example, the original diameter of the unformed cylindrical stop portions 38, 38' was assumed to be 0.049 in. (1.24 mm). For the original undeformed stop portion, as well as for the remaining cylindrical portion of the same member, theK moment of inertia was $2.83 \times 10^{-7}$ in.$^4$ about reference axes that are perpendicular to the longitudinal, central axis. Since the cross-sectional configuration of each of those portions is a circle, the moment of inertia is the same about all of such axes.

In the hypothetical construction shown in FIG. 6, the stop portion 38' has been deformed such that the lobes 40' extend outwardly a distance "A'" from the central, longitudinal axis. For exemplary purposes, the distance "A'" was assumed to be 0.0312 inch (0.78 mm) while the cross-sectional area in the X-Y plane was held constant at 0.0019 in.$^2$ (1.22 mm$^2$) (i.e., was the same both before and after deformation).

A calculation of the moment of inertia for the stop portion 38' revealed that the moment of inertia in a direction about the X axis, or "$I_{x'', was}$ 1.52×10$^{-7}$ in.$^4$. A calculation of the moment of inertia in a direction about the Y axis or "$I_y$", showed that the moment of inertia was 5.60×10$^{-7}$ in.$^4$. As can be appreciated, while the calculated moment of inertia about the Y axis, or "$I_y$" is relatively high for the stop portion 38', the moment of inertia in a direction about the X axis, or "$I_x$" is relatively low. As such, there is a risk that the stop portion 38' may bend or fracture when subjected to a relatively large force that is imposed on the stop portion 38' in directions about the X axis.

For the exemplary stop portion 38 shown in FIG. 5, the radius of the outer edge of the lobes 40 was assumed to be 0.0124 in. (0.315 mm), the radius of the concavity between the lobes 40 was assumed to be 0.0625 in. (1.587 mm) and the total cross-sectional area in the X-Y plane was assumed to be 0.0019 in.$^2$ (1.22 mm$^2$) (i.e., was equal to the cross-sectional area of the stop portion 38 before deformation).

The moments of inertia were then calculated in directions about two axes for the stop portion 38 as shown in FIG. 5. The calculated moment of inertia in a direction about the X axis, or "$I^x$", was 3.09×10$^{-7}$ in.$^4$. The calculated moment of inertia in a direction about the Y axis, or "$I_y$" was also 3.09×10$^{-7}$ in.$^4$. Moreover, all of the moments of inertia were found always to be the same value regardless of where the X and Y axes are oriented in FIG. 5. Such construction is an advantage, in that the rotative orientation of the member 34 need not be limited to certain positions for reasons of stiffness.

By comparing the calculated moments of inertia for the stop portion 38 to the calculated moments of inertia for the stop portion 38', it can be observed that the moments of inertia for the stop portion 38 are all higher than the smallest moment of inertia of the stop portion 38' (in this example, "$I_x$"). As a result, the second member 34 is less likely to bend or fracture when subjected to a force about the X axis in FIG. 5 the second member 34' when subjected to a force of equal magnitude about the X axis shown in FIG. 6. Consequently, the mechanism 10 is less likely to fail during the course of orthodontic treatment when equipped with the second member 34 instead of the hypothetical second member 34'.

Surprisingly, the calculated moments of inertia of the stop portion 38 are also higher than the moments of inertia for the cross-sectional shape of the cylindrical portion 36 as well as for the original, undeformed shape of the stop portion 38. As such, the second member 34 is stiffened by the stop portion 38. The advantage of the increased stiffness is provided even though a substantial deformation of the material and a significant change in the original shape of the material has occurred.

Figure 7:
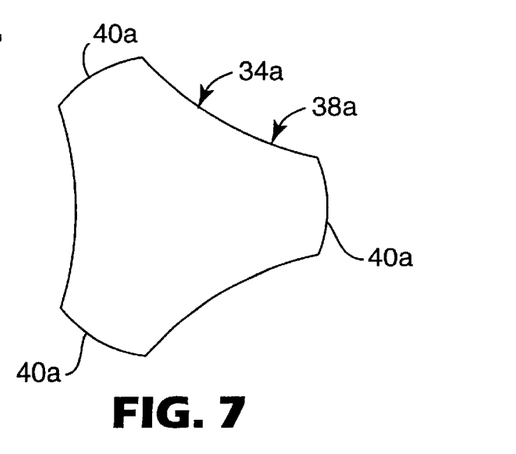
FIG. 7 is a view somewhat similar to FIG. 5 except that FIG. 7 illustrates a stop portion of a force module according to another embodiment of the invention.

Other options are also possible. For example, FIG. 7 illustrates an end cross-sectional view of a second member 34a according to another embodiment of the invention. The second member 34a includes a cylindrical portion as well as a stop portion 38a. The stop portion 38a is made of a formable material, and the stop portion 38a in this example also has three lobes 40a that are formed from the formable material.

The original shape of the stop portion 38a before deformation is similar to the shape of the adjacent cylindrical portion. In this embodiment, however, the lobes 40a are made using tooling that resists a free-form deformation such as the deformation shown in FIG. 5. Instead, the tooling used to make the stop portion 38a presses against the outer ends of the lobes 40a such that the resulting lobes 40a assume a somewhat different shape than the lobes 40 shown in FIG. 5.

Other variations are also possible. For example, the stop portion may include a number of lobes greater than three. However, the tooling needed to make such a construction is more complex than the tooling needed to make a stop portion with three lobes. Moreover, for some mechanisms it may be difficult to displace sufficient material to present a desired amount of interference for a positive stop in instances where more than three lobes are provided.

Figure 8:
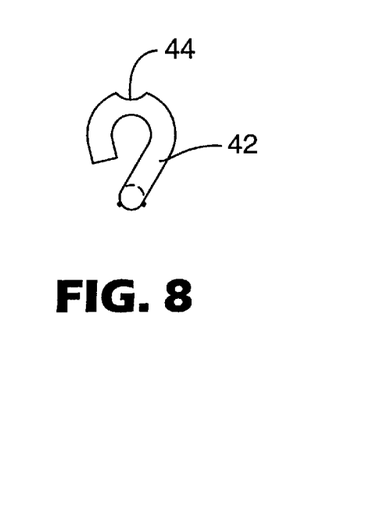
FIG. 8 is an enlarged end elevational view of the member alone that is shown in FIGS. 4 and 5.

Reference now is made again to FIGS. 2 and 3 for a description of remaining aspects of the mechanism 10. A first connector 42 is integrally connected to an outer end of the second member 34 and has a somewhat "C"-shaped configuration or hook-shaped configuration in end view. An end view of the first connector 42 is depicted in FIG. 8. The first connector 42 includes a groove 44 to facilitate bending of an outer end section of the connector 42 when desired.

The first connector 42 initially appears as shown in FIG. 8, and has an opening that is of sufficient size for receiving an archwire. Once the first connector 42 has been moved in place and surrounds the archwire, the outer end section of the connector 42 is bent toward the remaining portions of the connector 42 to a somewhat closed configuration. Further details regarding the connector 42 are provided in applicant's co-pending U.S. Patent Application entitled "COUPLING FOR ORTHODONTIC APPLIANCE", Ser. No. 09/687,392, filed Oct. 13, 2000 and which is expressly incorporated by reference herein.

The mechanism 10 also includes a third member 46 that is made of a section of tubular material having a cylindrical configuration. The third member 46 has an inner, narrowed end portion with an inner diameter that is slightly smaller than the outer diameter of the flared end of the first member 28. As such, the narrowed end portion of the third member 46 provides a limit for outward movement of the first member 28 in directions away from the third member 46.

A second connector 48 is secured to an opposite end of the third member 46. The second connector 48 includes a tubular segment that is secured to the third member 46 and also has an outwardly extending tab with a hole 50. The hole 50 receives a ball pin, a section of wire or other structure for securing the mechanism 10 to the chosen dental arch. In the example shown in FIG. 1, a pin 52 having an enlarged head is received in the hole 50, and is also bent at a right angle to extend through a passage in the upper buccal tube 20. An outer end of the pin 52 is bent in an arc to secure the pin 52 in place.

Preferably, the first connector 42 is connected to the lower archwire 24 by an attachment device 43. In brief, the attachment device 43 includes a first section with a passage for receiving the lower archwire 24 along with a second section that extends outwardly from the archwire 24. The second section includes an opening that pivotally receives the first connector 42. Additional aspects and features of the attachment device 43 are described in applicant's co-pending U.S. Patent Application entitled "ATTACHMENT DEVICE FOR INTRA-ORAL ORTHODONTIC APPLIANCE", U.S. Ser. No.______ [attorney docket no. 56889US002], which is filed on the same day as the present application and which is expressly incorporated by reference herein.

As illustrated in FIGS. 2 and 3, the mechanism 10 also includes a helical compression spring 54 that extends around the first member 28 and the third member 46. An outer end of the spring 54 bears against the fitting 30 and is located on a circular shoulder of the fitting 30 adjacent the first member 28. Optionally, the end of the spring 54 is welded to the fitting 30. An opposite end of the spring 54 bears against the second connector 48 that is secured to the outer end of the third member 46.

In FIG. 3, the second member 34 is illustrated as having reached a fully retracted position (i.e., has reached its inwardly limit of travel in a direction toward the second connector 48). As shown, the lobes 40 function as a stop and contact the end of the first member 28 inside of the fitting 30 to prevent further movement toward the second connector 48. FIG. 2 is an illustration of the second member 34 in an extended position relative to the first member 28, although other extended positions are also possible.

FIG. 1 illustrates the mechanism 10 as it appears when the patient's jaws are closed. As shown, the second member 34 has been moved to a fully retracted position such that the lobes 40 are in contact with the first member 28. Moreover, the first member 28 and the third member 46 have been moved toward each other against the bias presented by the spring 54 until the spring 54 is in a fully compressed orientation.

Additional features, options and principles of operation of the mechanism 10 are similar to those described in U.S. Pat. No. 5,964,588, which is expressly incorporated by reference herein.

Although the location of the stop portion 38 along the length of the second member 34 is fixed once it is made, it is possible for the practitioner to increase the amount of force presented by the mechanism if desired during the course of treatment. One method of increasing the force presented by the mechanism 10 is to install a sleeve of suitable length on the cylindrical portion 36 in a position between the fitting 30 and the stop portion 38. Optionally, the sleeve may be a split tube that is crimped in place, so that removal of the second member 34 from the first member 28 is unnecessary. As another example, the position or configuration of the pin 52 or the attachment device 43 may be modified as desired.

The stop portion 38 is useful in other orthodontic appliances as well. For example, the stop portion 38 may be used in a number of Herbst-type appliances that are known in the art.

Figure 9:
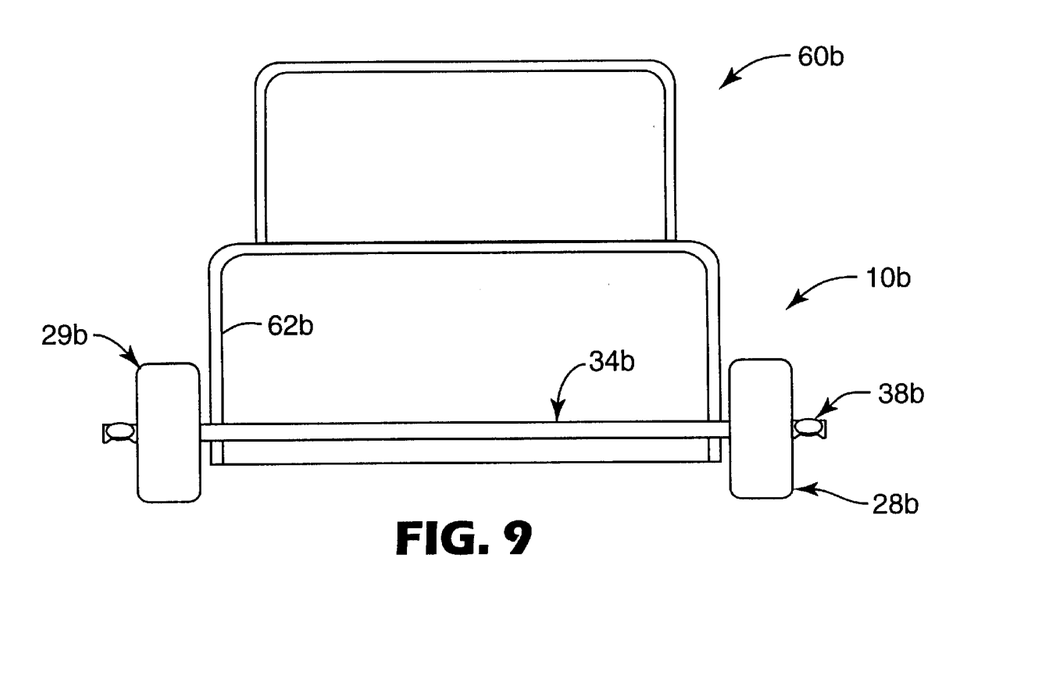
FIG. 9 is a side cross-sectional view of a mechanism according to yet another embodiment of the invention.

Another embodiment of the invention is illustrated in FIG. 9. In this embodiment, a mechanism 10b is part of a toy vehicle 60b. Examples of suitable vehicles include toy cars, toy trucks, toy trains and the like.

The mechanism 10b includes a first member 28b in the form of a wheel or tire. A second member 34b, in the shape of a shaft or axle, is received in a channel of the first member 28b. The first member 28b is freely rotatable about the longitudinal axis of the second member 34b so that the toy vehicle 60b can be rolled along a floor or other surface.

An outer end section of the second member 34b includes a stop portion 38b. The stop portion 38b is not shown in detail, but is similar to the stop portion 38 described above. In particular, the stop portion 38b includes three lobes that extend outwardly from the central longitudinal axis of the second member 34b. The lobes limit outward movement of the first member 28b in directions along the length of the second member 34b, so that the first member 28b does not disengage the second member 34b in use. Moreover, the presence of three lobes (instead of two) may facilitate rotation in instances where the members 28b, 34b are in contact with each other since the edges of the lobes present wider distributed areas for facilitating balanced, even engagement and reducing any tendency to bind.

In this example, the mechanism 10b also includes an additional first member 29b having a channel that receives an opposite end of the second member 34b. The additional first member 29b is optionally similar or identical to the first member 28b and is in the form of a wheel or tire. Furthermore, an adjacent outer end section of the second member 34b is provided with a stop portion that is similar to the stop portion 38b for limiting outward sliding movement of the additional first member 29b.

In the embodiment depicted in FIG. 9, the toy vehicle 60b has a body 62b with a pair of aligned holes or openings on opposite walls. The second member 34b is received in the openings. The body 62b consequently serves as a stop to limit sliding movement of the first members 28b, 29b toward each other along the length of the second member 34b.

A number of other variations are also possible. For example, the invention described above could be used for the manufacture of mechanisms that include pulleys, rollers, drums, or other components that rotate. Additionally, a rotation of 360 degrees or more is not necessary. For example, the mechanism could be useful in a pivoting mechanism that rotates through an arc of less than 360 degrees. As used herein, a "rotating"mechanism shall mean a mechanism having at least one member that pivots about an axis.

Other variations are also possible and will become apparent to those skilled in the art. Accordingly, the invention should not be deemed limited to the specific embodiments described above, but only by a fair scope of the claims that follow along with their equivalents.

What is claimed is:

1. A mechanism comprising:
   a first member having a channel; and
   a second member having a generally cylindrical portion at least partially received in the channel, the cylindrical portion having a longitudinal axis, the first member and the second member being movable relative to each other in directions along the longitudinal axis, the second member also having a stop portion for limiting relative movement between the first member and the second member in directions along the longitudinal axis, wherein the stop portion is made of a formable material and wherein the material is formed to present three lobes that extend outwardly in different respective directions from the longitudinal axis, and wherein the three lobes are located substantially equal distances apart from each other around the longitudinal axis.

2. A mechanism according to claim 1 wherein the lobes are arranged around the longitudinal axis such that the spaces between each adjacent pair of lobes are substantially equal to each other.

3. A mechanism according to claim 1 wherein the lobes extend outwardly in a radial direction equal distances from the longitudinal axis.

4. A mechanism according to claim 1 wherein the second member has a solid cross-section along a substantial majority of its length.

5. A mechanism according to claim 1 wherein the channel has a cylindrical configuration.

6. A mechanism according to claim 1 wherein the first member and the second member are pivotally movable relative to each other in directions about the longitudinal axis.

7. A sliding mechanism comprising:
   a receiving member having channel; and
   a plunger having a generally cylindrical portion at least partially received in the channel, the cylindrical portion having a longitudinal axis, the plunger and the receiving member being slidably movable relative to each other in directions along the length of the longitudinal axis, the plunger also having a stop portion for limiting relative sliding movement between the plunger and the receiving member, wherein the stop portion is made of a formable material and wherein the material is formed to present three lobes that extend outwardly in different respective directions from the longitudinal axis, and wherein the three lobes are located substantially equal distances apart from each other around the longitudinal axis.

8. A sliding mechanism according to claim 7 wherein the lobes are arranged around the longitudinal axis such that the spaces between each adjacent pair of lobes are substantially equal to each other.

9. A sliding mechanism according to claim 7 wherein the receiving member and the plunger are pivotally movable relative to each other in directions about the longitudinal axis.

10. A rotating mechanism comprising:
    a first member having a channel; and
    a second member having a generally cylindrical portion at least partially received in the channel, the cylindrical portion having a longitudinal axis, the first member and the second member being rotatable relative to each other in directions about the longitudinal axis, the second member also having a stop portion for limiting relative movement between the first member and the second member in directions along the longitudinal axis, wherein the stop portion is made of a formable material and wherein the material is formed to present three lobes that extend outwardly in different respective directions from the longitudinal axis, and wherein the three lobes are arranged around the longtudinal axis such that the spaces between each adjacent pair of lobes are substantially equal to each other.

11. A rotating mechanism according to claim 10 wherein the first member and the second member are slidable relative to each other in directions along the longitudinal axis.

12. A rotating mechanism according to claim 10 wherein the first member is a wheel and wherein the second member is an axle.

13. A rotating mechanism according to claim 10 wherein the mechanism is part of a toy vehicle.

14. A rotating mechanism according to claim 10 wherein the lobes extend outwardly equal distances from the longitudinal axis.

15. A rotating mechanism according to claim 10 wherein the second member has a solid cross-section along a substantial majority of its length.

16. A rotating mechanism according to claim 10 wherein the channel has a cylindrical configuration.

17. A rotating mechanism according to claim 10 wherein the first member and the second member are pivotally movable relative to each other along arcs that are greater than 360 degrees about the longitudinal axis.

18. An intra-oral force module for moving the relative positions of the upper and lower dental arches comprising:
    a first member having a channel; and
    a second member having a generally cylindrical portion at least partially received in the channel, the cylindrical portion having a longitudinal axis, the first member and the second member being slidable relative to each other in directions along the length of the longitudinal axis, the second member also having a stop portion for limiting relative sliding movement of the first member and the second member, wherein the stop portion is made of a formable material and wherein the material is formed to present three lobes that extend outwardly in different respective directions from the longitudinal axis, and wherein the three lobes are located substantially equal distances apart from each other around the longitudinal axis.

19. An intra-oral force module according to claim 18 and including a third member having a channel, wherein the first member is slidably received in the channel of the third member.

20. An intra-oral force module according to claim 19 wherein the first member and the third member have generally cylindrical configurations.

21. An intra-oral force module according to claim 19 and including a spring for urging at least two of the members in directions away from each other.

22. An intra-oral force module according to claim 21 wherein the spring extends externally around the third member and urges the first member and the third member in directions away from each other.

23. An intra-oral force module according to claim 18 wherein the lobes are arranged around the longitudinal axis such that the spaces between each adjacent pair of lobes are substantially equal to each other.

24. An intra-oral force module according to claim 18 wherein the lobes extend outwardly equal distances from the longitudinal axis.

25. An intra-oral force module according to claim 18 wherein the second member has a solid cross-section along a substantial majority of its length.

26. An intra-oral force module according to claim 18 wherein the channel has a cylindrical configuration.

27. An intra-oral force module according to claim 18 wherein the first member and the second member are pivotally movable relative to each other in directions about the longitudinal axis.

* * * * *

UNITED STATES PATENT AND TRADEMARK OFFICE
CERTIFICATE OF CORRECTION

PATENT NO.   : 6,589,051 B2 Page 1 of 1
DATED        : July 8, 2003
INVENTOR(S)  : Cleary, James D.

It is certified that error appears in the above-identified patent and that said Letters Patent is hereby corrected as shown below:

Column 6,
Line 54, "thek" should read -- the --.

Column 7,
Line 1, " "$l_{x}$, was" should read -- "$l_x$", was --.
Line 21, " "$1^x$," should read -- "$l_x$" --.
Line 37, insert -- than -- preceding "the".

Column 10,
Line 64, insert -- a -- following "having".

Signed and Sealed this

Twenty-first Day of October, 2003

JAMES E. ROGAN
*Director of the United States Patent and Trademark Office*